US006586723B2

(12) United States Patent
Moran et al.

(10) Patent No.: US 6,586,723 B2
(45) Date of Patent: Jul. 1, 2003

(54) SENSOR CABLE

(75) Inventors: Christopher Raymond Moran, Dumbarton (GB); Walter Craig Michie, Glasgow (GB)

(73) Assignee: University of Strathclyde, Glasgow (GB)

(*) Notice: Subject to any disclaimer, the term of this patent is extended or adjusted under 35 U.S.C. 154(b) by 148 days.

(21) Appl. No.: 09/878,844

(22) Filed: Jun. 11, 2001

(65) Prior Publication Data

US 2002/0071113 A1 Jun. 13, 2002

(30) Foreign Application Priority Data

Jun. 10, 2000 (GB) .............................. 0014126

(51) Int. Cl.[7] .................................................. G01J 1/04
(52) U.S. Cl. .......................... 250/227.16; 250/227.14; 385/13
(58) Field of Search ................. 250/227.11, 227.14, 250/227.15, 227.16; 385/12, 13, 102, 128, 141; 356/437, 439, 440

(56) References Cited

U.S. PATENT DOCUMENTS

| | | | | |
|---|---|---|---|---|
| 4,463,254 A | * | 7/1984 | Asawa et al. | 250/227.16 |
| 4,812,014 A | | 3/1989 | Sawano et al. | |
| 5,378,889 A | * | 1/1995 | Lawrence | 250/227.16 |

FOREIGN PATENT DOCUMENTS

| | | |
|---|---|---|
| DE | 9319610 | 3/1994 |
| EP | 0 490 849 B1 | 11/1995 |
| WO | WO 94/18536 | 8/1994 |
| WO | WO 95/08838 | 3/1995 |

OTHER PUBLICATIONS

Copy of Search Report for GB0114159.7 completed Feb. 11, 2002.

* cited by examiner

Primary Examiner—Kevin Pyo
(74) Attorney, Agent, or Firm—Alston & Bird LLP

(57) ABSTRACT

A detection system for use in detecting the presence of a non-aqueous organic measurand is provided. The system comprises a fiber-optic probe assembly incorporating an optical fiber which is susceptible to micro bending anywhere along its length, and a body of material contained within a rigid containment structure, wherein said body comprises a material selected from the group consisting of a rubber, plastic and semi-crystalline/rubbery polymeric material which is subject to a volumetric change capable of inducing a microbend in said optical fiber in the presence of said non-aqueous organic measurand and wherein the body of material is a substantially continuous coating which has a thickness prior to contact with the non-aqueous measurand of less than 7.5 mm and a sensor assembly coupled to the probe assembly, the sensor assembly having optical signal transmitting and receiving means arranged to identify optical fiber microbend changes arising, in use, from forces imposed locally on the fiber by the interaction of the rigid containment structure and volumetric changes in the body of material.

24 Claims, 7 Drawing Sheets

SENSOR CABLE

The present invention relates to a detection system for use in detecting the presence of a non-aqueous organic measurand, such as a hydrocarbon. One example is to detect the leaking of crude oil from a pipeline.

WO94/18536 describes a system for detecting the presence of an aqueous measurand. The system includes a fibre-optic probe assembly which incorporates an optical fibre, a thin film of a water swellable hydrogel and a rigid containment structure. The hydrogel is in contact with the optical fibre such that a volumetric change in the hydrogel causes a microbend of the optical fibre which is detected by a sensor assembly coupled to the probe assembly by means of optical time domain reflectometry (OTDR).

However, the system described in WO94/18536 is only for the detection of aqueous target measurands which serve to swell a responsive hydrogel material and as such are sensitive only to water-containing measurands. Moreover, the hydrogel block copolymers disclosed therein have a high degree of hydrogen bonding and can therefore be susceptible to the Marangoni effect (see below).

WO95/08838 discloses a method and apparatus for detecting the presence of a liquid or vapour hydrocarbon analyte. The apparatus employs discrete units of silicone rubber to absorb hydrocarbons and thus expand. However, to allow sufficient expansion of the absorber-expander material for detection, the material is typically in the range of 10 mm or more in diameter. Furthermore, calibration of the apparatus is necessary and since it is not possible to produce a continuous coating due to cost, the spatial sensitivity is dependent on the spacing of the discrete units of silicone rubber.

It is an object of the present invention to provide a detection system which is capable of detecting the presence of a wide variety of non-aqueous organic measurands.

According to the present invention, there is provided a detection system for use in detecting the presence of a non-aqueous organic measurand, said system comprising: a fibre-optic probe assembly incorporating an optical fibre which is susceptible to micro bending anywhere along its length, and a body of material contained within a rigid containment structure, wherein the body of material comprises a rubber, plastic or semi-crystalline/rubbery polymeric material which is subject to a volumetric change capable of inducing a microbend in said optical fibre in the presence of said non-aqueous organic measurand and wherein the body of material is a substantially continuous coating which has a thickness prior to contact with the non-aqueous measurand of less than 7.5 mm;

and a sensor assembly coupled to the probe assembly, the sensor assembly having optical signal transmitting and receiving means arranged to identify optical fibre microbend changes arising, in use, from forces imposed locally on the fibre by the interaction of the rigid containment structure and volumetric changes in the body of material.

Substantially continuous coating is understood to refer to a coating of material comprising a rubber, plastic or semi-crystalline/rubbery polymeric material which covers more than 50%, preferably more than 65%, and most preferably, more than 80% of the surface of a former or optical fibre.

The system may be used simply to detect the presence of a target measurand at an unspecified location along the length of the optical fibre, though it is preferred that said signal transmitting and receiving means is also capable of detecting the particular location on the optical fibre where the signal carrying property of the optical fibre has changed and thus also detecting the particular location of the affected portion of the body of material (which is preferably elongate).

In a modification, the system may have more than one probe assembly in which case the sensor assembly is provided with a logic function output circuit to decipher the effects of different target measurands on the different polymers of the different probe assemblies.

The body of material may be extended to form a continuous rod or may be deposited as a coating on a former or the optical fibre. The thickness of the rod or coating is less than 7.5 mm, such as less than 1 mm, for example less than 200 $\mu$m or even 50 $\mu$m. Preferably the rod or coating is continuous with the length of optical fibre, thereby enabling extremely accurate detection of a microbend of the optical fibre and positioning of the non-aqueous organic measurand ingress.

The body of material may expand on exposure to one target measurand, and may contract on exposure to another target measurand to be detected.

The exposure of the body of material to a target measurand may result in a permanent change in volume, or the material may return to its original configuration on removal of the target measurand.

Preferably also, the rubber, plastic or semi-crystalline/rubbery polymeric material has chemical characteristics tailored to provide responsiveness to the target measurand.

The body of material may comprise a second component, said component being tailored to provide responsiveness to the target measurand. The second component can either through interaction with the rubber, plastic or semi-crystalline/rubbery polymeric material, or alone, be subject to volumetric change on exposure to said target measurand.

Preferably also, the containment structure comprises a sheath which may be braided for externally protecting the optical fibre and the body of material from external disturbance, which sheath is porous to allow the body of material to be exposed to the target measurand. Alternatively, the sheath may be non-porous but sacrificially corrodible in the presence of the target measurand.

If the signal transmitting and receiving means produces pulses of optical energy into the optical fibre the backscattered energy resulting from such microbends may be measured as a function of time, or distance travelled along the fibre length. This technique is known as Optical Time Domain Reflectometry (OTDR), and an earlier application of OTDR is described, for example, in EPA 0 490 849.

The optical fibre is preferably bound to the body of material, which is preferably elongate, by an inelastic third member. Most preferably, the third member is thread-like in form. With this arrangement, expansion or contraction of a portion of the body of material causes the thread-like member to bite into, or relax its grip on the optical fibre at one or more distinct locations, thus increasing or decreasing the microbends formed in the optical fibre by the thread-like member and facilitating detection and location of the presence of the target measurand.

The sensor assembly may utilise a continuous coating of an organic measurand (eg. fluid or vapour swellable) rubber, plastic or semi-crystalline/rubbery polymeric material system along the entire length of an optical fibre. This is achieved by either coating the absorbent material directly onto the optical fibre or by attaching a separate, coated former or rod along the entire length of the optical fibre. As the coating or attached coated former/rod is continuous along the length of the optical fibre, the complete length of the sensing cable will be responsive to the presence of an organic measurand. The coating is not sensitive to and does not swell to any significant degree in water or other aqueous measurands. Thin responsive coatings (e.g. <50 or <200 microns) will give a rapid detecting response in the order of seconds or minutes. However, in some situations, thicker coatings (>200 microns) may be used where a larger microbending response is desired, in which case the time of the detection response will be in the order of minutes to hours. By carefully selecting the absorbent polymeric material, it is possible to detect almost any organic measurand.

As an example, polymeric materials in contact with chemically and thermodynamically compatible organic liquids, initially, absorb and swell with the molecules of the organic liquid to form a swollen gel. The swelling of the material is accompanied by a volumetric expansion.

The swelling of a material in a liquid is commonly expressed in terms of parts per hundred (pph) relative to the initial dry weight of the material. It may also be expressed as a percentage swelling with respect to the swollen material. The two terms can be defined using the following equations:

$$\text{Swelling Uptake, pph} = \frac{\text{Swollen Weight} - \text{Dry Weight}}{\text{Dry Weight}} \times 100$$

$$\text{Swelling Content, \%} = \frac{\text{Swollen Weight} - \text{Dry Weight}}{\text{Swollen Weight}} \times 100$$

Since the polymer-polymer intermolecular forces are high because of, for example, crosslinking, crystallinity, complexation, strong hydrogen bonding or chain entanglement, the swollen polymer gel does not dissolve. Similarly, atmospheres rich in the vapour of volatile organic liquids also produce swelling and volumetric expansion of appropriate polymeric materials. The swelling of polymeric materials with organic fluids produces a volumetric expansion that can be used to exert a mechanical force or pressure which in combination with an optical fibre system can be used as a means for the detection of organic fluids. The extent of the mechanical response will be largely dependent on the degree to which the material absorbs and swells in the organic fluid and on the mechanical strength and/or modulus of the swollen gel. This response is reversible by evaporation of the organic liquid/vapour from the swollen material.

The concept of polymer/solvent solubility parameters (an empirical guide to thermodynamic compatibility) is used to help determine the selection of suitable polymeric systems capable of swelling in specific organic fluids and vapours. The solubility parameter, $\delta$, is the square root of the cohesive energy density of a molecule. For relatively small molecules such as solvents (and most organic fluids and vapours), the cohesive energy density is equivalent to the energy of vapourisation per unit volume. For polymers, the cohesive energy density is determined using the molar attraction constants, E, of the different structural components of the polymer;

$$\delta = \frac{p \sum E}{M}$$

where values of E are summed over the structural configuration of the repeating unit in the polymer chain, with repeat molecular weight M and density p. Solubility can be expected, in the absence of strong interactions such as hydrogen bonding, if the difference between the $\delta$ values for the solvent ($\delta_1$) and the polymer ($\delta_2$) is less than ~2.0 $(\text{cal/cm}^3)^2$ (~4.0 $(\text{Mpa})^2$), but not if it is appreciably higher.

Similarly, solubility parameter values, $\delta$, are calculated for potential polymeric coating systems and also for the organic fluid or vapour target measurands. As the polymer coatings on the sensor cable are chemically crosslinked or effectively crosslinked through chain-entanglement, complexation or other physical interactions, swelling rather than dissolution occurs when the material is exposed to a fluid or vapour with a closely matching solubility parameter. Again, it is stressed that the solubility parameter approach is useful only in the absence of strong polymer-solvent interactions and is to be used only as a guide to the potential swellability of a polymeric coating. Careful experimentation using swellability tests provide the best indication as to whether or not a particular polymeric coating system is suitable for inducing the reversible microbending of an optical fibre after exposure to specific organic fluids and vapours.

Solubility parameter theory also provides a useful guide for the selection of solvents for the application of polymeric coatings from organic solutions. When polymeric coatings are applied from an organic solution, the Marangoni effect is frequently observed whereby the polymer appears to present an increasing surface tension as the coating solution increases in concentration by solvent evaporation. This produces the effect of the formation of thicker and thinner sections of the coating especially when the single step application of thicker coatings is attempted. The Marangoni effect is often most pronounced when coating with block copolymers that contain a significant proportion of hydrogen bonding. The Marangoni effect is removed by selecting a solvent in which the solubility parameter and hydrogel bonding characteristics of the sensing polymer are close to that of the evaporating solvent and not deviating from this by more than 2 $(\text{cal/ml})^{0.5}$. Either higher or lower $\delta$ values can provoke the Marangoni effect. A higher value for the solvent tends to give a better resolution of Marangoni unevenness than a lower value. In the case of rubbers and non hydrogen bonded block copolymers the Marangoni effect is removed by selecting solvents with a higher $\delta$ than the polymers so that concentration of the solution leads to a decreased surface tension and more even film formation. The prevention of the Marangoni effect is of increasing importance where thick coatings are required.

Many of the polymeric materials suitable for this type of sensing cable are commercially available and can be coated onto a fibre or cable by standard techniques such as extrusion or by coating from liquid or solution. The coating may require a subsequent curing step, e.g. exposure to heat, radiation or atmospheric moisture. Materials suitable for the rod or coating can be found in common polymer science and technology textbooks e.g. *Textbook of Polymer Science*, F. W. Billmeyer, JR., John Wiley & Sons Inc., 1971, *The Handbook of Elastomers*, Eds. A. K. Bhowmick & H. L. Stephens, Marcel Dekker Inc., 1988 and *The Chemistry of Organic Film Formers*, D. H. Solomon, John Wiley & Sons Inc., 1967.

The properties of such materials include high elongation tensile strength and be capable of being coated onto an optical fibre. Examples of suitable active materials are hydrocarbon rubbers such as natural rubber, butyl rubber, ethylene-propylene rubber (EPDM) rubber, chlorinated hydrocarbon rubbers, nitrile rubbers, silicone rubbers, acrylic rubbers, sulphur based rubbers, styrene-acrylonitrile and styrene-butadiene rubbers and block copolymers, polyurethane, polyamide, polybutadiene, polyisoprene and modified polyethylene elastomers. Additionally, virtually any paint formulations can be utilised for the sensor. For example, lacquers such as nitrocellulose, cellulose acetate or related derivatives, vinyl chloride copolymers, methyl methacrylate copolymers, epoxy resins and polyurethanes which can be crosslinked by e.g. reaction with atmospheric moisture, di- or polyamines or polyols and oil-based alkyd resins which can be air dried. Such materials can be heat cured. Polymers with the capability of swelling in specific organic fluids can also be specially designed and synthesised. The minimum required swelling expansion to produce a measurable microbend is approximately 5 microns. The extent of the expansion will be determined by the swellability of the polymeric coating in a particular organic fluid and can be controlled by varying the coating thickness. The polymeric coatings can be designed to be thin (e.g. <200 $\mu$m or <50 $\mu$m, or values in between) to give a faster response.

The polymeric coatings may in some cases be applied from an organic solution but are, after solvent evaporation, insoluble and swellable in the organic fluids to be detected. The coatings may also be applied using organic solutions which are subsequently rendered insoluble but swellable in organic fluids and vapours through solvent evaporation or crosslinking reactions.

The organic solutions used in the coating process may be designed, by careful solvent selection, to provide more even film formation and avoidance of the Marangoni effect. The coatings may be applied by dipping in the liquid form of the coating running through a hole at the bottom of a feeding cup, spraying powder coating from a heated fluidised bed, melt extrusion around the fibre or onto a support, direct extrusion (co-extrusion onto a support rod or filament or directly onto the optical fibre) or forming a fibre and radially wrapping the fibre around the fibre-optic cable. The coating may require a subsequent curing or crosslinking stage for example, by reaction with atmospheric moisture or other chemical agents, exposure to radiation (e.g. UV and gamma irradiation), and heat (e.g. thermally induced crosslinking and/or elimination of a volatile inhibitor) to form a coating that is insoluble but swellable in specific organic fluids and vapours.

The crosslinking or curing of the coating systems is dependent on the nature of the selected active coating material. However, not all coating systems will require a post-coating crosslinking or curing stage i.e. it is not always necessary for a coating to be crosslinked for it to be swellable in a target organic fluid. The coating may be effectively crosslinked@ through physical interactions such as entanglement, complexation, hydrogen bonding and the phase separation of the polymer chain components into chemically and thermodynamically incompatible domains or phases. For example, a block or graft copolymer coating could be applied from solution or by melt extrusion. If the individual polymeric blocks are incompatible, then a phase separated domain morphology may be established. A block or graft copolymer coating of this type may be able to swell but not dissolve when exposed to an organic fluid that is compatible with one (or more) of the polymer phases or domains. The polymer phases that are incompatible with the organic fluid will maintain the mechanical integrity of the swollen coating. These basic principles will be known to those skilled in the art of polymer science and technology. However, not all the materials of this type will be suitable for use in the proposed sensor cable.

There are many techniques that can be used for chemically crosslinking or curing polymer coatings and again these will be known to those skilled in the art of polymer science. These methods are described in detail in general and specific polymer science textbooks, academic publications and product literature. Common methods include the reaction of polymers and monomers with polyfunctional crosslinking agents, the reaction and crosslinking of functional groups contained in the polymer chains, reaction with atmospheric moisture or other chemical agents, and radiation and thermally induced crosslinking of polymer chains.

For example, suitable coating material is the rapid curing, solvent dispersible EP4412 Silastic Compound (Dow Corning). This is known as a Aone component@ addition cure silicone rubber compound and can be easily dissolved and dispersed in a range of solvents including methyl ethyl ketone, toluene, xylene, chloroform, dichloromethane and cyclohexane. Films and coatings can be prepared by solvent-evaporation followed by curing at 160–180° C. The compound contains a volatile inhibitor which is rapidly driven off at elevated temperatures (>120° C.). The curing or crosslinking rate is dependent on the film or coating thickness but is in the range of 15–30 seconds for thickness of 50–200 microns.

With careful selection of the absorbent polymeric material, it is possible to detect almost any organic fluid or vapour. This includes any liquid or volatile non-aqueous organic materials which present a potential spillage hazard in the chemical industry or other industries. For example, products from the petrochemical, coal based chemical and natural products chemical manufactures, hydrocarbon fuel and oil storage facilities and pipelines, cable oils used in the power industry and the common organic fluids and solvents e.g. hydrocarbon liquids, chloroform, dichloromethane, carbon tetrachloride, phenol and substituted phenols, toluene, benzene, dodecyl benzene, cyclohexane, acetone, diethyl ether, petroleum ethers, liquid ethers and esters, methyl ethyl ketone and other liquid ketones, methanol, ethanol, isopropanol and other alcohols, etc. Also included is the extractive industry for natural oils used in large quantities in food stuffs and cosmetic applications. These are commonly triglycerides which can present a considerable fire hazard when a spillage occurs.

The interaction (swelling) with the sensing polymer is largely dependent on the thermodynamic compatibility or match (lack of match) of their cohesive densities. The thermodynamic compatibility of a liquid and a polymer is often expressed empirically using solubility parameter theory where the solubility parameter is defined as the square root of the cohesive energy density. A match or near match of the solubility parameters of the target liquids and the sensor coating materials will, generally, indicate the potential sensing capability of the sensor cable.

The sensor cable can be protected from the environment using porous metallic sheathing of the type common to the cabling industry. Sheathing made from synthetic and natural fibres and fabrics (wrapped or braided), and porous polymer tubing that is inert to the target organic fluids can also be used. Sacrificial sheathing in the form of a tube, coating or wrapping could be fabricated using polymers that are selected to be soluble in the target organic fluids.

Embodiments of the present invention will now be described by way of example, with reference to the accompanying drawings in which.

Figure 1:
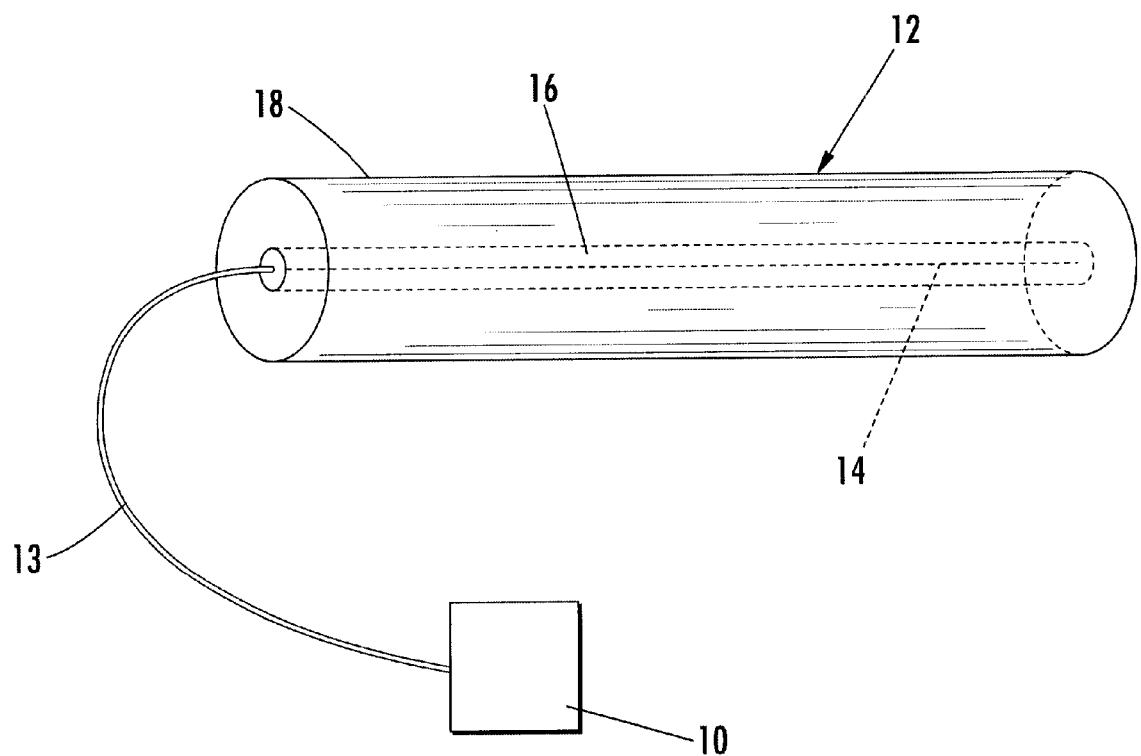
FIG. 1 is a somewhat schematic view of a detection system according to the present invention.

FIG. 1 of the drawings illustrates a detecting system which comprises a sensor assembly 10 coupled via an optical fibre 13 to a fibre optic probe assembly 12 wherein a length of optical fibre 14, at least in use (as will be explained), is subject to microbending at intervals along its length. Fibres 13 and 14 are preferably identical. The sensor assembly 10 includes an optical signal transmitter and receiver and operates as an Optical Time Domain Reflectometer (OTDR). The operation of the OTDR 10 is described more fully in EP0490849. Within the probe assembly 12, the optical fibre 14 is arranged in association with a body of material 16 and a rigid containment structure 18 in a geometrical configuration such that under exposure to the measurand of interest on permeation of the structure 18, the optical fibre 14, is mechanically disturbed, either creating a new microbend or changing an existing microbend so as to exhibit a change in its loss characteristics local to the point of measurand influence. In accordance with the present invention the body of material 16 is selected to comprise an organic fluid or vapour swellable polymer.

Various geometrical embodiments of the sensor assembly of the present invention are possible. Typical embodiments are described in detail in WO94/18536 to which the skilled reader is directed.

EXAMPLE 1

A variety of non-aqueous organic swellable materials may be used in the detecting system described in Example 1.

Figure 2:
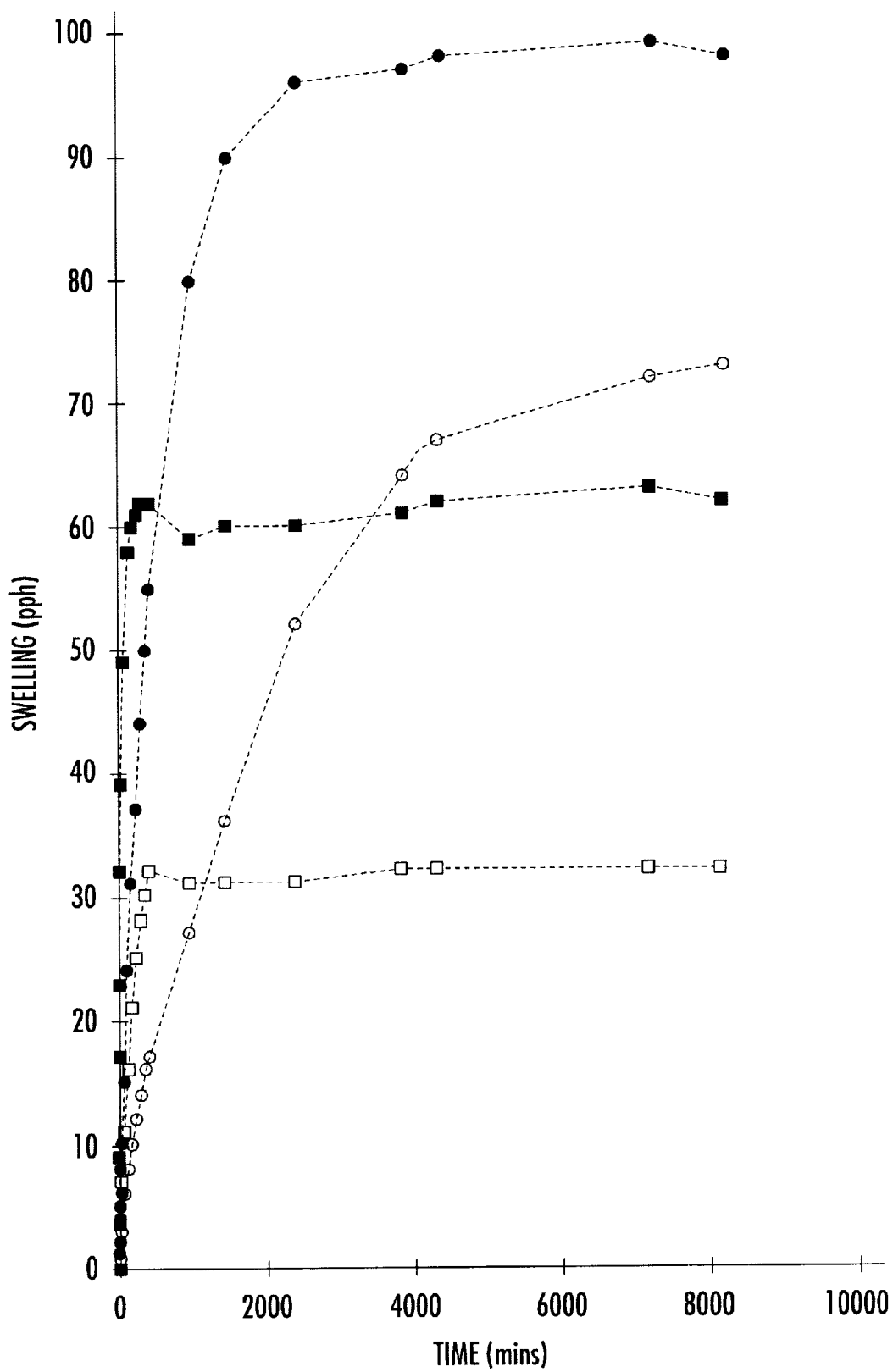
FIG. 2 is a graph showing the swelling response of a range of rubber film samples in diesel oil at 21° C. (--N--Butyl Rubber(IIR), Thickness: 1.90 mm, --$--Ethylene-Propylene Rubber(EPDM), Thickness: 1.50 mm, --R--Natural Rubber (NR), Thickness: 1.15 mm, --P--Silicone Rubber(SIR), Thickness: 0.80 mm).

FIG. 2 illustrates the swelling response of a range of rubber films that were equilibrated in a sample of commercial diesel oil. All of the rubber film samples used in the diesel oil swelling experiments were obtained from commercial suppliers and have been prepared using a variety of standard techniques used in the rubber industry for forming films.

Small film samples were cut from each of the rubber films and the un-swollen dimensions and weights recorded. The film samples were then immersed in diesel oil at ambient temperature. Periodically, the samples were removed from the oil, blotted with tissue paper and weighed on an electronic balance. This procedure was repeated until the swollen weight became constant. The swelling isotherms for the rubber films in diesel oil can be determined using the previously described swelling equations. The rubber films in this experiment were relatively thick (500 micron) compared to the proposed sensor cable coating thickness of 50–200 microns. As the rate of swelling is proportional to the square of the thickness, thin coatings of the order of 50–200 microns would be expected to produce a measurable swelling response in around 10 seconds –10 minutes. A 500 micron thick coating of a Dow Corning medical grade silicone elastomer (Silastic 500-5) gave an equilibrium swelling response in diesel oil of ~65 pph. The film was 75% swollen after 30 minutes.

The swelling of 200 $\mu$m thick films of the Silastic EP4412 silicone rubber and Silastic 9280/30E liquid silicone rubber (both Dow Corning products) in a range different hydrocarbon liquids at ambient temperature was investigated. The rate and extent of swelling depended on various properties and interactions (for example, molecular weight, viscosity, thermodynamic compatibility, temperature, etc.). Some of the materials were very volatile and this affected the accuracy of the swelling measurements. The data, presented in Tables 1 and 2 demonstrates the potential for rapid response using materials in thin film form. Within 5 minutes, the film samples were between 75–95% of their maximum swelling in the different hydrocarbon liquids. An accurate study of the swelling isotherms between 0–5 minutes has still to be performed. The lower molecular weight, lower viscosity, more volatile liquids were observed to swell significantly in 10 s of seconds (kerosene, petrol, condensate). Again, the speed of response is proportional to the square of the thickness and so thickness' of 0.50 $\mu$m and 0.100 $\mu$m will respond and swell more rapidly.

TABLE 1

Swelling of Silastic EP4412 Silicone Rubber Film (200$\mu$m)

in Hydrocarbon Liquids
Uptake of Hydrocarbon Liquid (pph)

| Time (mins) | Kerosene | Petrol | Diesel | Gas Oil | Condensate | Dodecyl Benzene |
|---|---|---|---|---|---|---|
| 5 | 154 | 191 | 74 | 60 | 182 | 52 |
| 10 | 160 | 192 | 81 | 68 | 190 | 61 |
| 20 | 159 | 196 | 81 | 68 | 182 | 65 |
| 30 | 162 | 191 | 83 | 69 | 190 | 65 |
| 60 | 165 | 199 | 82 | 69 | 194 | 66 |

TABLE 2

Swelling of Silastic 9280/30E Silicone Rubber Film (200$\mu$m) in Hydrocarbon Liquids Uptake of Hydrocarbon Liquid (pph)

| Time (mins) | Kerosene | Petrol | Diesel | Gas Oil | Condensate | Dodecyl Benzene |
|---|---|---|---|---|---|---|
| 5 | 144 | 179 | 72 | 51 | 156 | 47 |
| 10 | 151 | 167 | 78 | 60 | 162 | 56 |
| 20 | 147 | 187 | 78 | 64 | 177 | 60 |
| 30 | 155 | 192 | 80 | 67 | 164 | 64 |
| 60 | 152 | 189 | 79 | 66 | 177 | 64 |
| 120 | 157 | 188 | 81 | 67 | 180 | 64 |

Of the silicone rubber compounds investigated, the Silastic EP4412 and Silastic 9280/30E demonstrate the best potential for use in the production of the sensor. The properties of these compounds (unswollen) are listed in Table 3.

TABLE 3

| Property | Silastic EP4412 | Silastic 9280/30E |
|---|---|---|
| Hardness | 45–55 IRHD | 32 IRHD |
| Specific Gravity | 1.13–1.19 g/cm$^3$ | 1.13 g/cm$^3$ |
| Tensile Strength | 8.5 Mpa | 8.1 Mpa |
| Elongation at Break | 750% | 900% |
| Tear Strength | 20 kN/m | 20 kN/m |

With respect to mechanical strength in a swollen state, a qualitative assessment indicated that the EP4412 silicone rubber is significantly stronger than the 9280/30E silicone rubber. In comparison with other silicone rubbers, the combination of relative properties such as high hardness, high tensile strength, high elongation at break and high tear strength appear to indicate the significant retention of mechanical integrity in the swollen state.

In terms of applicability in thin film form, the one component Silastic EP4412 compound which is designed to be organic solvent dispersible for coating processes clearly has the best properties for use in the sensor construction. The 2 component liquid silicone rubber Silastic 9280/30E is highly viscous and not easily applied at thicknesses of 200 μm and below.

The rate of swelling is clearly dependent on the sample thickness and the maximum swelling varies from rubber to rubber. The swelling potential of a range of plastic and rubber materials was assessed by simple swelling studies of this type in different organic liquids and vapours at different temperatures. These results can be used to determine whether the material is suitable for use in the design of the sensor.

EXAMPLE 2

Microbending Capability of Polymer Films Exposed To Organic Liquids

Figure 3:
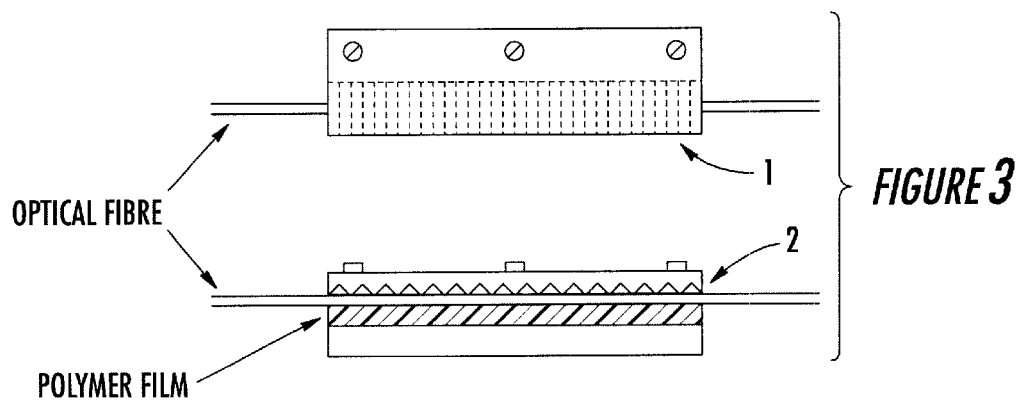
FIG. 3 illustrates an original microbending transducer design in accordance with an embodiment of the present invention.
Figure 4:
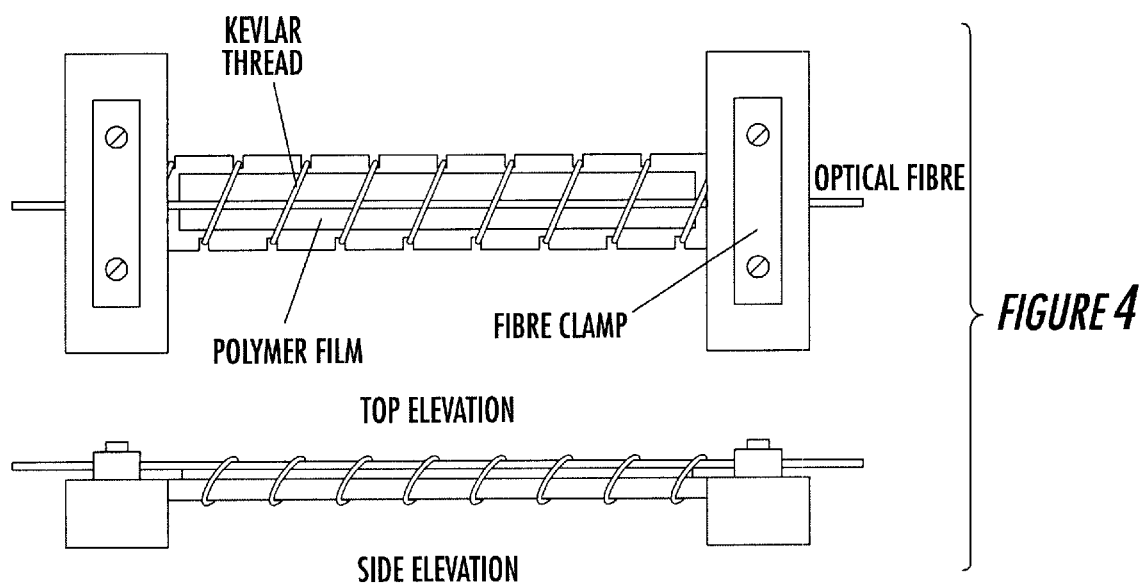
FIG. 4 illustrates a revised microbending transducer design in accordance with an embodiment of the present invention.

The ability of polymer films to exert a swelling force capable of inducing the detectable microbending of an optical fibre was demonstrated using the microbending transducer units (1, 2) shown in FIG. 3 and FIG. 4.

The microbending response was monitored by inserting a polymer film into the microbending transducer unit and then pouring an appropriate, thermodynamically compatible organic liquid (i.e. a liquid that will swell the polymer film) onto the unit. The swelling induced microbending response was measured using an OTDR.

Figure 5:
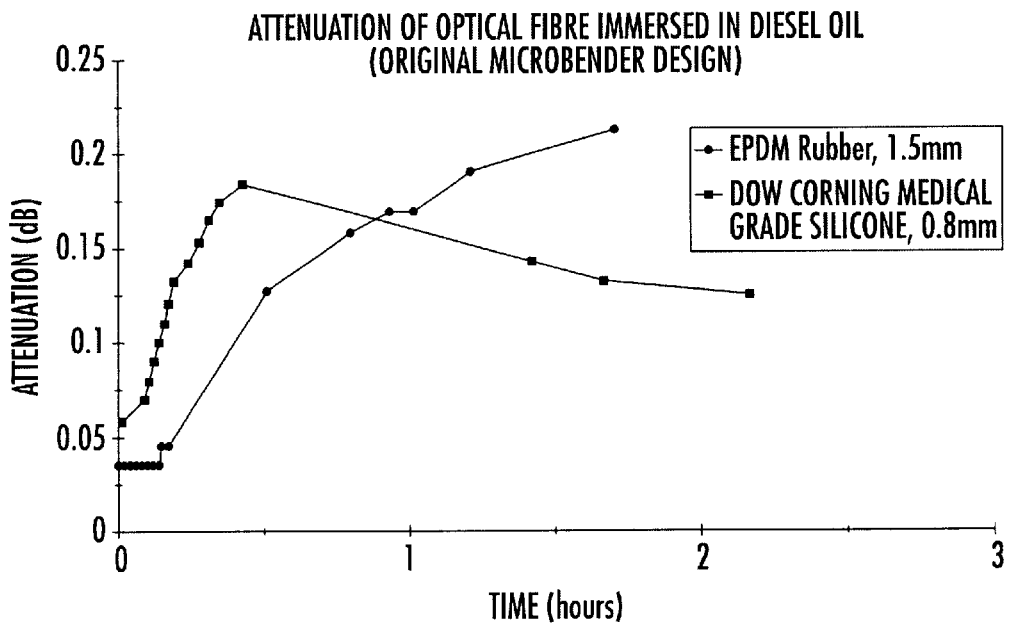
FIG. 5 is a graph illustrating the attenuation of an optical fibre incorporated in the microbending transducer design of FIG. 3 and immersed in diesel oil.
Figure 6:
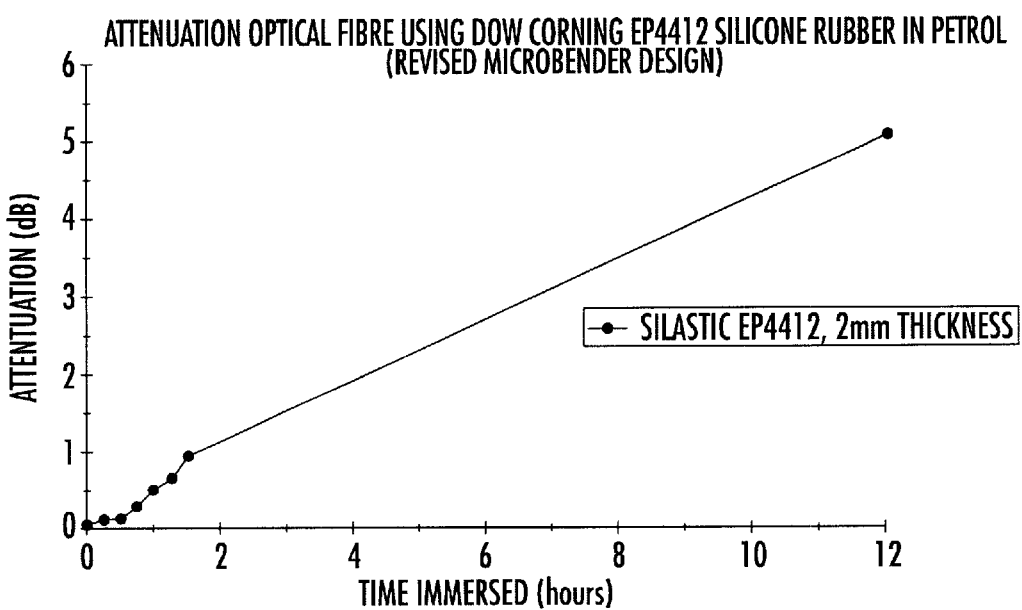
FIG. 6 is a graph illustrating the attenuation of an optical fibre incorporated in the microbending transducer design of FIG. 4.

The results for various rubber films are shown in FIGS. 5 and 6, in which it could be seen that the polymer films were capable of exerting swelling forces capable of inducing the detectable microbending of optical fibres after exposure to appropriate organic liquids. The speed and extent of the response was proportional to the thickness and swellability of the polymer film.

FIG. 5 shows the attenuations obtained for a medical grade silicone rubber (Dow Corning) and an EPDM rubber, exposed to diesel oil and using the original microbending transducer unit design (1). FIG. 6 shows the attenuation obtained for the Dow Corning Silastic EP4412 silicone rubber, exposed to petrol and using the revised microbending transducer unit (2). The greater thickness of the EP4412 film combined with the increased swellability of the material in petrol produces a higher attenuation compared to the thinner, lower swelling films in diesel oil.

EXAMPLE 3

The Operation Of The Organic Fluid Sensor Cable

Figure 7:
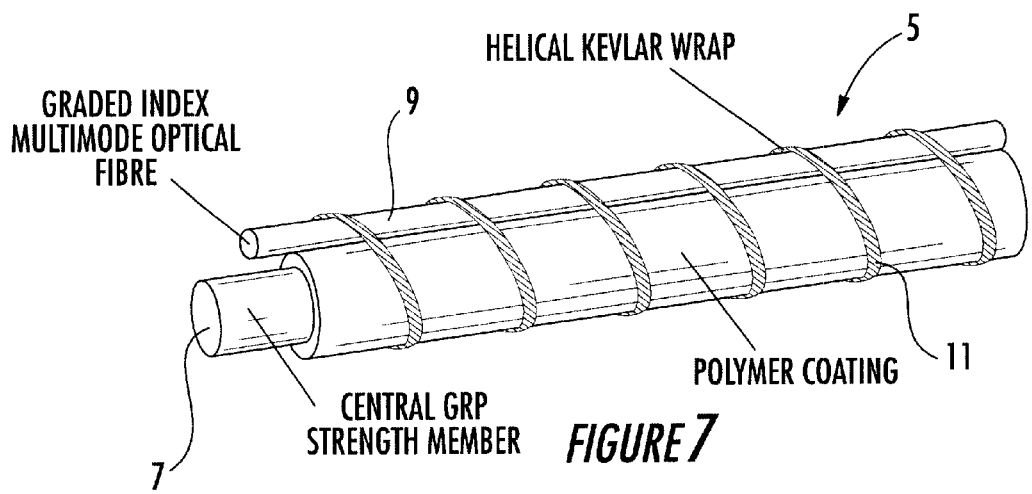
FIG. 7 is a diagram illustrating the construction of a sensor cable according to an embodiment of the present invention.

The construction of an optical fibre microbending sensor cable for the detection of organic fluids is shown in FIG. 7 (generally denoted as 5).

The sensor (5) was manufactured using a 0.9 mm diameter GRP central core (7) with 50 μm thick crosslinked silicone rubber (Varflex Corporation, 512 West Court Street, Rome, N.Y. 13440, USA). The optical fibre (9) was a 62.5/125 PCVD graded index multimode optical fibre. The pitch of the microbending Kevlar thread wrap (11) was 1.0 mm. The sensor length was approximately 1 km.

Figure 8:
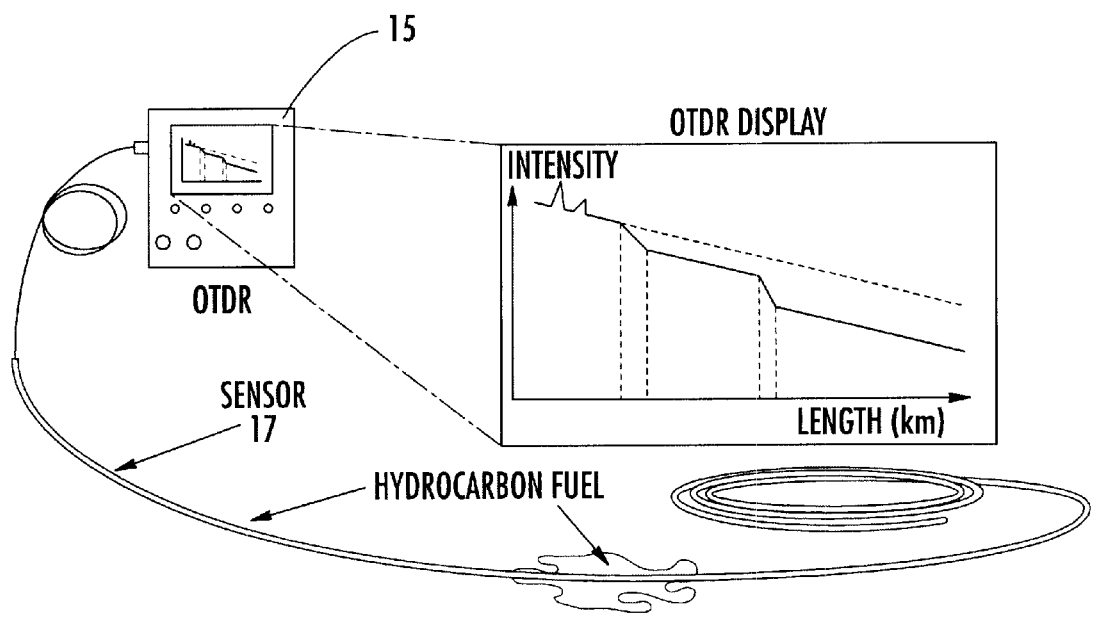
FIG. 8 is a diagram illustrating an experimental layout of two events on a sensor cable.

A schematic of the experimental layout for evaluating the sensor response is shown in FIG. 8.

The OTDR used in the tests was a Nortech Fibronic Inc. (Formerly Antel, Quebec, Canada) AOE50 unit (15), using a pulse width of 20 ns (equivalent to an approximately 2 meter resolution).

Figure 9:
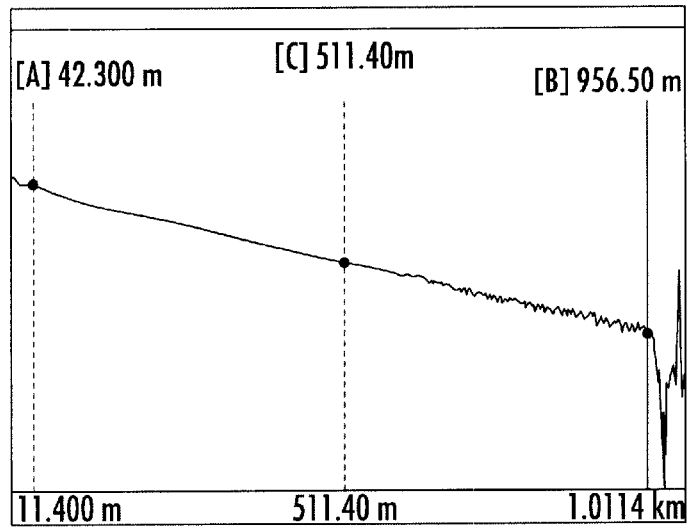
FIG. 9 is an OTDR trace of a sensor cable of length of 1 km.

The dry attenuation of a sensor (17) was measured as approximately 10 dB/km which was close to the ideal design value of 4–5 dB/km. Despite the high magnitude, the attenuation reading appeared consistent over the entire length, indicating that the tension of the Kevlar thread was well controlled. A short section of the sensor at the far end exhibited high loss, eliminating the possibility of interrogating the sensor from both ends. The OTDR trace for this sensor length is shown in FIG. 9.

Figure 10:
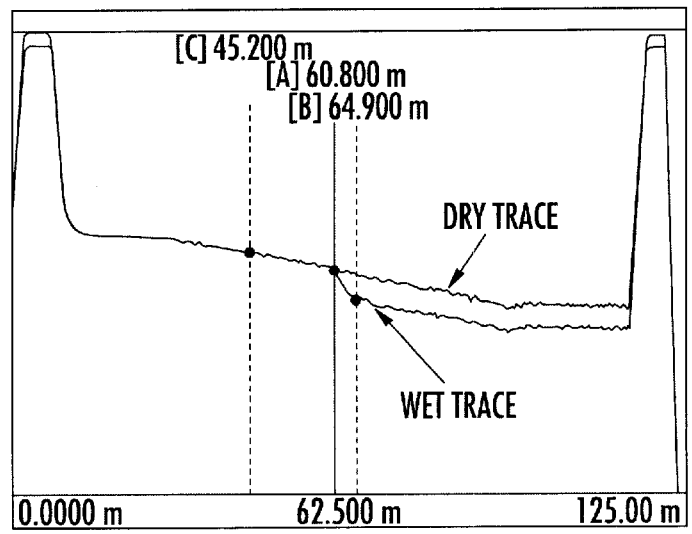
FIG. 10 is an OTDR trace of a 1 m section of a 70 m sensor which is either dry or wet.

A 70-meter section of sensor was removed from the main reel for evaluation purposes and fusion spliced onto a 30-meter patch-cord. Coiling the sensor into a smaller diameter increased the dry attenuation from 10 to approximately 20 dB/km. A central section of this sensor was located and a 1 meter length exposed to petrol (BP Unleaded Motor Spirit, BS EN 228). After 30 seconds exposure the sensor displayed a visible change in attenuation, corresponding to ~0.5 dB drop in the signal over a measured length of 4 meters. This is equivalent to an approximate attenuation of 125 dB/km. FIG. 10 displays both the dry and 1 meter wet traces for this 70 meter sensor.

Figure 11:
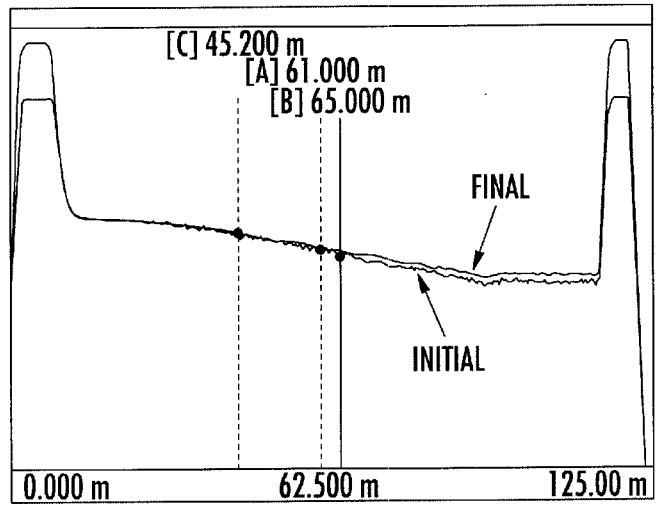
FIG. 11 is an OTDR trace showing initial dry loss and dry loss after exposure.

The petrol was allowed to evaporate and the attenuation of the affected section compared with the initial dry value of 22 dB/km. A reduction to 17 dB/km had occurred in the dry attenuation due to the swelling and subsequent evaporation of the fuel. The reduction in the attenuation was most likely due to settling of the optical fibre and Kevlar into the silicone coating. The traces for the initial dry attenuation and the dry attenuation after exposure and evaporation are shown in FIG. 11.

Figure 12:
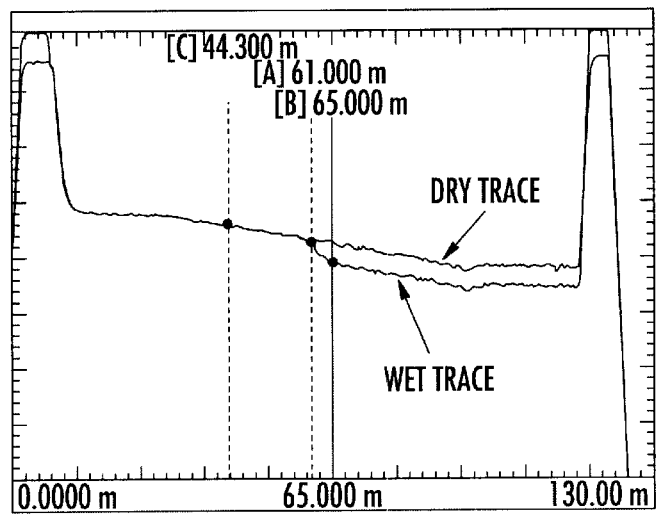
FIG. 12 is an OTDR trace of a second exposure an initial dry reading.

The test was repeated and in the second case the sensor displayed a drop of 0.4 dB/km for the same wetted section when exposed to petrol. This is shown in FIG. 12, superimposed on the dry attenuation trace (before exposure was initiated). The results of these initial tests indicated that there was a small drop in the sensitivity after the sensor has been activated. However, the sensor appears to be capable of rapidly (seconds) and repeatedly (cycleable) detecting the exposure to an organic liquid.

Applications for this type of sensing cable can be identified in the chemicals and petroleum industries, fuel/oil storage facilities and fuel/oil pipelines. Many applications will require that the sensor cable will not respond to the presence of water or aqueous media but only to the presence of organic fluids or vapours.

It will be understood that the principal advantage of the present invention is the ability to detect and locate a wide variety of organic fluids and vapours emanating from, for example, a fault in a pipeline or a storage tank.

Furthermore, the apparatus incorporating optical fibre, a swellable material and a braided sheath can be made at one location employing extrusion technology.

In addition to these, the thin coating of swellable material will result in reduced cost and greater spatial accuracy.

What is claimed is:

1. A detection system for use in detecting the presence of a non-aqueous organic measurand, said system comprising:
    a fibre-optic probe assembly incorporating an optical fibre which is susceptible to micro bending anywhere along its length, and a body of material contained within a rigid containment structure, wherein said body comprises a material selected from the group consisting of a rubber, plastic and semi-crystalline/rubbery polymeric material and which is subject to a volumetric change capable of inducing a microbend in said optical fibre in the presence of said non-aqueous organic measurand and wherein the body of material is a substantially continuous coating which has a thickness prior to contact with the non-aqueous measurand of less than 7.5 mm;
    and a sensor assembly coupled to the probe assembly, the sensor assembly having optical signal transmitting and receiving means arranged to identify optical fibre microbend changes arising, in use, from forces imposed locally on the fibre by the interaction of the rigid containment structure and volumetric changes in the body of material.

2. A detection system according to claim 1, wherein said body of material is a substantially continuous coating on a former.

3. A detection system according to claim 2, wherein substantially continuous coating covers more than 50% of the body of a former or said optical fibre.

4. A detection system according to claim 3, wherein said substantially continuous coating covers more than 80% of the body a former or said optical fibre.

5. A detection system according to claim 1, wherein said body of material contained within the rigid containment structure is extended to form a continuous rod on a former or the optical fibre.

6. A detection system according to claim 1, wherein the thickness of said body of material is less than 200 $\mu$m.

7. A detection system according to claim 6, wherein the thickness of said body of material is less than 50 $\mu$m.

8. A detection system according to claim 1, wherein said body of material expands on exposure to a target measurand.

9. A detection system according to claim 1, wherein said body of material contracts on exposure to a target measurand.

10. A detection system according to claim 1, wherein exposure of said body of material to a target measurand results in a permanent change in volume.

11. A detection system according to claim 1, wherein exposure of said body of material returns to its original configuration on removal of the target measurand.

12. A detection system according to claim 1, wherein said body of material has chemical characteristics tailored to provide responsiveness to the target measurand.

13. A detection system according to claim 1, wherein said body of material comprises a second component, said component being tailored to provide responsiveness to the target measurand.

14. A detection system according to claim 13, wherein said second component is subject to a volumetric change on exposure to said target measurand through an interaction with said body of material.

15. A detection system according to claim 13, wherein said second component is alone subject to a volumetric change on exposure to said target measurand.

16. A detection system according to claim 1, wherein said containment structure comprises a braided sheath for externally protecting the optical fibre and the body of material from external disturbance, and wherein said braided sheath is porous to allow said body of material to be exposed to the target measurand.

17. A detection system according to claim 1, wherein said containment structure comprises a non-porous sheath which is sacrificially corrodible in the presence of the target measurand.

18. A detection system according to claim 1, wherein said system has more than one probe assembly to detect more than one target measurand and a logic function output circuit for deciphering the effects of said different target measurands on the different polymers of said different probe assemblies.

19. A detection system according to claim 1, wherein said optical signal transmitting and receiving means is also capable of detecting the particular location on the optical fibre where the signal carrying property of the optical fibre has changed and thus also detecting the particular location of the affected portion of the body of material.

20. A detection system according to claim 19, wherein said signal transmitting and receiving means uses Optical Time Domain Reflectometry.

21. A detection system according to claim 1, wherein said optical fibre is bound to said body of material, which is elongate, by an inelastic third member.

22. A detection system according to claim 21, wherein said inelastic third member is thread-like in form.

23. A detection system according to claim 1, wherein said rubber, plastic or semi-crystalline/rubbery polymeric material is selected from the group consisting of hydrocarbon rubbers such as natural rubber, butyl rubber, ethylene-propylene rubber (EPDM) rubber, chlorinated hydrocarbon rubbers, nitrile rubbers, silicone rubbers, acrylic rubbers, sulphur based rubbers, styrene-acrylonitrile and styrene-butadiene rubbers and block copolymers, polyurethane, polyamide, polybutadiene, polyisoprene, modified polyethylene elastomers, nitrocellulose, cellulose acetate or related derivatives, vinyl chloride copolymers, methyl methacrylate copolymers, epoxy resins and polyurethanes.

24. A detection system according to claim 1, wherein said non-aqueous organic measurand is selected from the group consisting of hydrocarbon liquids, chloroform, dichloromethane, carbon tetrachloride, phenol and substituted phenols, toluene, benzene, dodecyl benzene, cyclohexane, acetone, diethyl ether, petroleum ethers, liquid ethers and esters, methyl ethyl ketone and other liquid ketones, methanol, ethanol, iso-propanol and other alcohols and triglycerides.

* * * * *

UNITED STATES PATENT AND TRADEMARK OFFICE
Certificate

Patent No. 6,586,723 B2

Patented: July 1, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Christopher Raymond Moran, Dumbarton, United Kingdom; Walter Craig Michie, Glasgow, United Kingdom; Brian Culshaw, Kilmacolm, United Kingdom; Neil Bonnette, Graham, Glasgow, United Kingdom.

Signed and Sealed this Twenty-fourth Day of May 2005.

DAVID P. PORTA
*Supervisory Patent Examiner*
Art Unit 2878